(12) United States Patent
Masson et al.

(10) Patent No.: US 7,022,069 B1
(45) Date of Patent: Apr. 4, 2006

(54) CIRCUMFERENTIAL RETRACTOR APPARATUS WITH LOCKING SLOTS

(75) Inventors: Marcos V. Masson, Houston, TX (US); Mark H. Henry, Houston, TX (US)

(73) Assignee: SI-1, Inc., Conroe, TX (US)

( * ) Notice: Subject to any disclaimer, the term of this patent is extended or adjusted under 35 U.S.C. 154(b) by 0 days.

(21) Appl. No.: 10/078,321

(22) Filed: Feb. 20, 2002

Related U.S. Application Data

(63) Continuation-in-part of application No. 09/916,819, filed on Jul. 30, 2001.

(51) Int. Cl.
*A61B 1/32* (2006.01)

(52) U.S. Cl. .................. 600/217; 600/206; 600/210; 600/219

(58) Field of Classification Search .......... 600/201, 600/206, 210, 213, 217, 219, 226, 227, 229, 600/235, 237
See application file for complete search history.

(56) References Cited

U.S. PATENT DOCUMENTS

| | | | | |
|---|---|---|---|---|
| 170,573 | A | * 11/1875 | Lesh | 267/74 |
| 1,389,436 | A | * 8/1921 | Cameron | 600/219 |
| 2,695,607 | A | * 11/1954 | Hipps et al. | 600/210 |
| 3,762,401 | A | * 10/1973 | Tupper | 600/217 |
| 4,559,677 | A | * 12/1985 | Tracy | 24/300 |
| 5,307,790 | A | * 5/1994 | Byrne | 600/206 |
| 5,520,610 | A | 5/1996 | Giglio | |
| 5,716,328 | A | * 2/1998 | Grieshaber et al. | 600/206 |
| 5,931,777 | A | 8/1999 | Sava | |
| 5,964,697 | A | 10/1999 | Fowler | |
| 5,964,698 | A | * 10/1999 | Fowler | 600/217 |
| 6,074,343 | A | 6/2000 | Nathanson et al. | |
| 6,090,043 | A | 7/2000 | Austin et al. | |
| 6,117,072 | A | 9/2000 | Fowler, Jr. | |
| 6,409,731 | B1 | * 6/2002 | Masson et al. | 606/86 |

OTHER PUBLICATIONS

"Retractor Hooks attache to elastic coupler", Surgical Products, Oct. 1999, p. 1.
"Surgical Retractor Hooks", Orthopedic Technology Review, Jan. 2000, and Apr. 2000.
"The Lone Star Retractor System", Journal of Hand Surgery, Jan. 2000.
"The Lone Star Retractor System", Outpatient Surgery Magazine, Jan. 2000, Feb., 2000, and Apr. 2000.
"Retract with Ease", Outpatient Surgery Magazine, May 2000.
"The Lone Star Retractor System", Foot & Ankle, Jan. 2000 and Feb. 2000.

\* cited by examiner

*Primary Examiner*—Pedro Philogene
*Assistant Examiner*—David A Bonderer
(74) *Attorney, Agent, or Firm*—Browning Bushman P.C.

(57) ABSTRACT

A circumferential retractor apparatus including a first retractor paddle, a second retractor paddle and an elastic member. Each of the first and second retractor paddles includes a body portion with an arm extending outwardly therefrom. The arm supports a grasping surface. The arm of the retractor paddle has a hole formed therein through which the elastic member passes. A slot opens at a top edge of the body portion such that a respective end of the elastic member is received therein. The slot has a dog leg configuration with a wide opening adjacent the top edge of the body portion of the respective paddles.

15 Claims, 2 Drawing Sheets

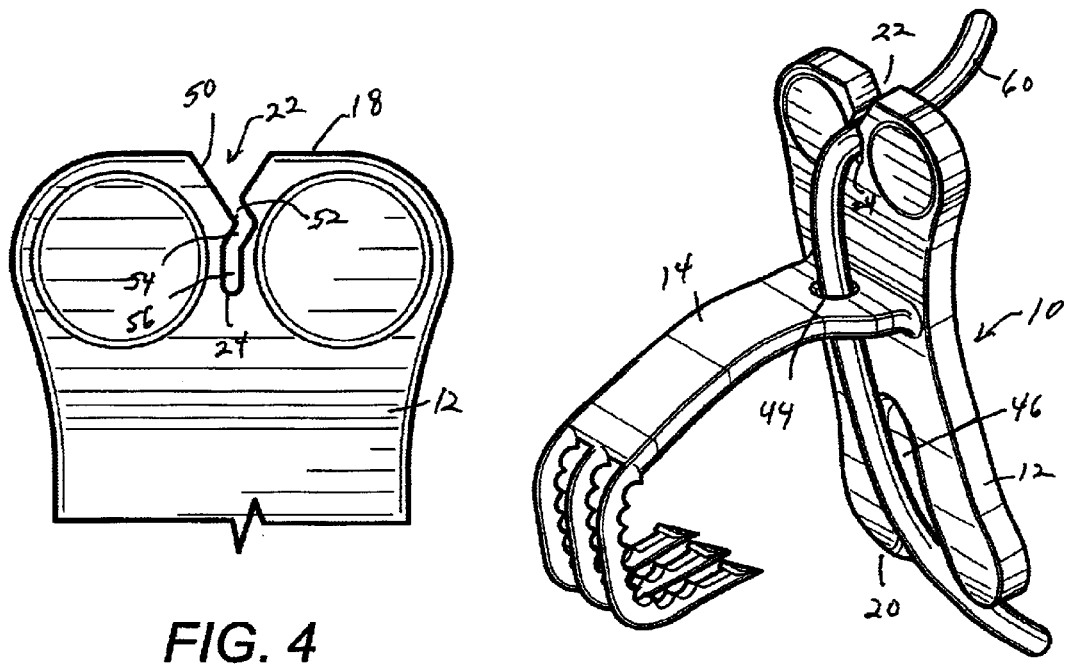
FIG. 4
FIG. 5
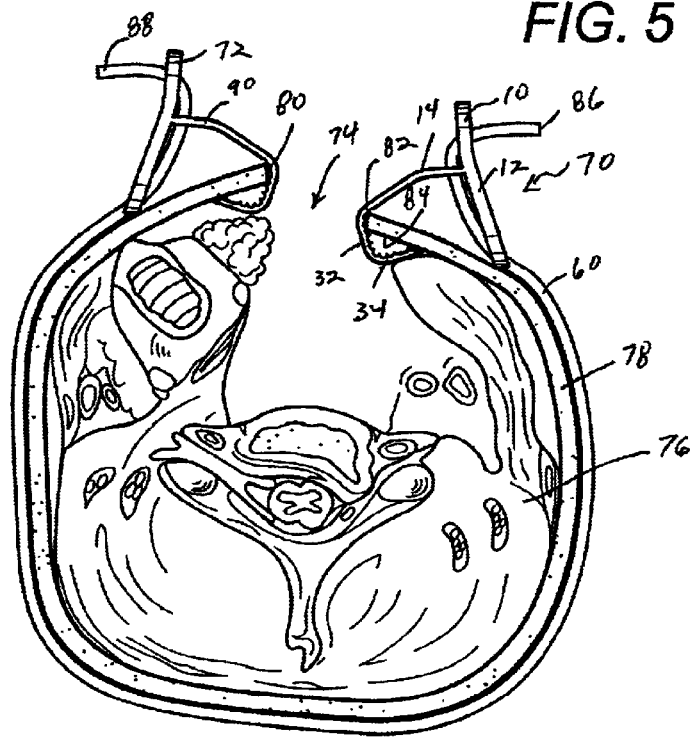
FIG. 6

CIRCUMFERENTIAL RETRACTOR APPARATUS WITH LOCKING SLOTS

CROSS REFERENCE TO RELATED APPLICATIONS

The present application is a continuation-in-part of U.S. patent application Ser. No. 09/916,819, filed on Jul. 30, 2001, and entitled "CIRCUMFERENTIAL RETRACTOR APPARATUS", presently pending.

BACKGROUND OF THE INVENTION

1. Field of the Invention

The present invention relates to surgical retractors. More particularly, the present invention relates to circumferential retractors. In particular, the present invention relates to circumferential retractors having a surgical tubing-receiving slot which locks in the ends of the surgical tubing.

2. Description of Related Art

Surgical "retraction" is the drawing back of body tissue. When the operation involves making an incision, the incision itself often must be retracted. During surgery, internal organs, bones and tissues are intermittently retracted through the opening created in the retracted incision.

In certain surgeries, an assistant's fingers are used as retractor paddles. However, greater technical ease is available through the use of various mechanical retractor systems. Mechanical retractor systems can be divided into two major groups: externally mounted "fixed" to the operating table and self-retaining retractors.

The mechanical systems attached to the operating table present the same type of physical obstruction to the surgeon's movement as presented by the assistant's body, arms and hands since the externally fixed retractor systems of a vertical column, supporting arm(s) or ring and retractor paddles attached thereto. The retractor paddles, support arms or ring and vertical column in these apparatus are adjustable in multiple planes and axes of motion; however, these retractor paddles are not all independently adjustable in the vertical plane. Movement of a support arm or ring of these apparatus necessitates movement of all retractor paddles attached thereto.

Ideally, mechanical retractors, both externally mounted and self retaining, need to provide for internal organ and tissue retraction, be quickly and easily assembled, positioned and repositioned in all planes and axes of motion, present as little obstruction to the surgeon's movement as possible, protect the sterile field, diminish the risk of tissue trauma and yet be stable enough to function adequately while reducing the need for assistance.

Self-retaining retractors that have attempted to provide for internal organ and tissue retraction through the open incision have failed to permit quick, independent, easy and safe adjustment of internal organ and tissue retractor paddles in all planes and axes of motion, and in effect the prior art is either ineffectual or unsafe, or both since these paddles are not easily adjustable in the vertical plane and such internal organ and tissue retractor paddles must traverse over (or through) internal tissue before reaching the desired location along the retractor handle and/or frame. The retractor paddle depth is not highly variable and the retractor paddles location on the retractor frame is limited.

In the past, various patents have issued relating to such retractors. For example, U.S. Pat. No. 5,520,610, issued on May 28, 1996 to Giglio, describes a self-retaining retractor. This retractor includes flexible, resilient retractor paddles which can be placed into the incision. A rigid frame is provided which includes two interlocking halves laid longitudinally over the incision. The incision retractor paddles are manually clipped to each frame half, and then the frame halves are opened to the desired extent. The incision retractor paddles and the frame provide the apparatus with stability for retraction of internal organs and tissues through the open incision by the addition of mounting jigs containing adjustment posts onto mounting means which radiate outwardly from the frame.

U.S. Pat. No. 5,931,777, issued on Aug. 3, 1999 to G. A. Sava, teaches a tissue retractor with particular use in spinal surgery. This tissue retractor includes a pair of pivotally linked arms, each with a blade mounted thereto by a ball-and-socket joint so as to allow free movement of the blades relative of the arms. The blades have an anchoring end to anchor to the bone. The retractor is operable by placing the blades in a wound opening, securing the anchoring ends to a portion of the bone in a position apart from each other, and operating the retractor to cause the blades to separate and to retract tissues surrounding the wound opening by outward pivoting of the blades relative to the position of the anchoring ends.

U.S. Pat. No. 6,074,343, issued on Jun. 13, 2000 to Nathanson et al., describes a surgical tissue retractor comprised of a plurality of retractor blades that can be operated simultaneously. Right and left retractor blades are mounted on an actuator mechanism that spreads or expands the blades as a rotatable primary actuator knob is rotated. A third retractable arm is mounted for simultaneous operation with the right and left retractor blade or independent operation through a secondary rotatable actuator knob that extends or retracts a threaded shaft attached to the center retractor blade.

U.S. Pat. No. 6,090,043, issued on Jul. 18, 2000 to Austin et al., describes a tissue retractor including a hook, a handle and an elastomeric band. The hook has a tissue-engaging portion and is retained by the handle such that the tissue engaging portion extends from a first end of the handle. The handle end of the band is retained by a second end of the handle. The back has a longitudinal body and at least one hub disposed about the body.

The parent application of the present application, i.e. U.S. application Ser. No. 09/619,819, describes a surgical retractor apparatus having a first retractor paddle with a grasping surface and a body portion supporting the grasping surface, a second retractor paddle having a grasping surface and a body portion supporting the grasping surface, and an elastic member having one end received by the first retractor paddle and an opposite end received by the second retractor paddle. Each of the paddles has a hole formed therein of a size suitable for allowing the elastic member to pass therethrough. A slot is formed in the body portion so as to open toward the hole. The slot is of a tapered configuration so as to have a wide end opening to the hole and a narrow end away from the hole. The grasping surface includes a plurality of fingers extending outwardly of the body portion. Each of the plurality of fingers are arranged in parallel spaced relationship to each other. The elastic member is a length of surgical tubing.

In this prior art application by the present inventors, several improvements were noted as being possible. After experimentation with this invention, it was found that a better locking slot could be configured so as to prevent any accidental release of the surgical tubing from the slot. This releasing action could occur if the locked-in tubing were accidentally bumped such that the tubing was released from the slot. Also, certain orientations of the grasping surface with respect to the incision could cause the tubing to deflect in a manner which made locking less easy and less secure. As such, a need developed so as to provide an improved locking feature for the retractor paddle. Additionally, a need developed so as to have an orientation between the grasping surface and the locking slot which maintained the grasping surface in a proper orientation while assuring a proper locking of the elastic surgical tubing within the slot.

It is an object of the present invention to provide a retractor paddle for a circumferential retractor which positively locks the surgical tubing within a slot.

It is another object of the present invention to provide a retractor paddle for a circumferential retractor apparatus wherein the arrangement of the locking slot and tubing properly orients the grasping surface toward the incision.

It is a further object of the present invention to provide a retractor paddle for a circumferential retractor apparatus which prevents the accidental release of the surgical tubing from the locking slot.

It is still a further object of the present invention to provide a circumferential retractor apparatus which properly maintains the incision in an open position.

It is another object of the present invention to provide a circumferential retractor apparatus which minimizes damage to the tissues along the edges of the incision.

It is a further object of the present invention to provide a circumferential retractor apparatus which can provide immediate feedback to the surgeon as to the amount of tension that is applied to the retracted tissues.

It is a further object of the present invention to provide a circumferential retractor apparatus which is securely supported on the skin.

It is still a further object of the present invention to provide a circumferential retractor apparatus which is easy to use, relatively inexpensive and easy to manufacture.

It is still a further object of the present invention to provide a circumferential retractor apparatus which is disposable.

These and other objects and advantages of the present invention will become apparent from a reading of the attached specification and appended claims.

BRIEF SUMMARY OF THE INVENTION

The present invention is a circumferential retractor apparatus comprising a first retractor paddle having a grasping surface, a second retractor paddle having a grasping surface, and an elastic member having one end received by the first retractor paddle and an opposite end received by the second retractor paddle. The first retractor paddle has a body portion with an arm extending outwardly therefrom. The arm serves to supporting the grasping surface. Similarly, the second retractor paddle also includes a body portion with an arm extending outwardly therefrom. The arm of the second retractor paddle also supports the grasping surface.

In the present invention, each of the arms of the first and second retractor paddles has a hole formed therein. The elastic member has one end extending through the hole of the first retractor paddle and an opposite end extending through the hole of the second retractor paddle. The body portion of each of the first and second retractor paddles includes a top edge and a bottom edge. The arm extends outwardly between the top edge and the bottom edge. The body portion of each of the retractor paddles includes a slot which opens at the top edge. This slot is suitably tapered so as to have a wide opening at the top edge and narrowing downwardly therefrom. The slot has a dog leg shape extending downwardly from the top edge.

The body portion of each of the retractor paddles has an indented area adjacent to the bottom edge. This indented area faces the arm of the respective retractor paddles. Portions of the tubing will extend through the indented area in the space between the surface of the indented area and the skin of the patient. One end of the elastic member is affixed within a bottom of the slot away from the top edge of the body portion.

In the present invention, the grasping surface of each of the retractor paddles includes a plurality of fingers which extend outwardly of the arm. The arm extends generally transverse to the body portion of the respective retractor paddle. Each of these plurality of fingers comprises a first section connected to the arm and extending transversely downwardly therefrom and a second section extending transversely inwardly from an end of the first section opposite the arm. Each of the first and second sections has an interior surface. This interior surface has a plurality of ribs extending outwardly therefrom. The second section has an inward end. Each of the plurality of fingers at the inward end has an arrowhead member at this inward end.

In the preferred embodiment of the present invention, the elastic member is a length of surgical tubing. The first retractor paddle should have an identical configuration to the second retractor paddle.

BRIEF DESCRIPTION OF THE SEVERAL VIEWS OF THE DRAWINGS

FIG. 4 is a detailed view showing the dog leg-shaped slot associated with the retractor paddle of the present invention.

FIG. 5 is a perspective view of surgical tubing as passed through and locked in place with the retractor paddle of the present invention.

FIG. 6 shows the circumferential retractor apparatus of the present invention as utilized a with an incision.

DETAILED DESCRIPTION OF THE INVENTION

Figures 1, 2:
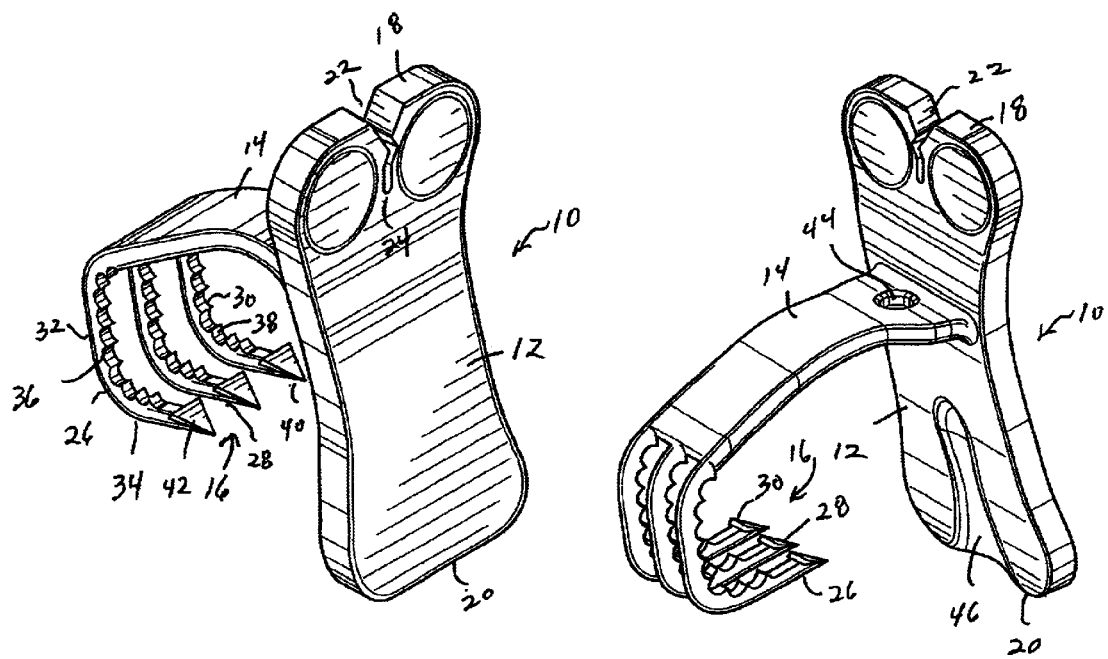
FIG. 1 is a perspective view of a retractor paddle of the circumferential retractor apparatus of the present invention.
FIG. 2 is another perspective view of the retractor paddle as used in the circumferential retractor apparatus of the present invention.

Referring to FIG. 1, there is shown a retractor paddle 10 for a circumferential retractor apparatus in accordance with the teachings of the preferred embodiment of the present invention. The retractor paddle 10 includes a body portion 12 having an arm 14 extending outwardly therefrom. The arm 14 supports a grasping surface 16. The body portion 12, the arm 14 and the grasping surface 16 are integrally formed of a polymeric material.

Importantly, as shown in FIG. 1, the body portion 14 has a roughly rectangular configuration having a top edge 18 and a bottom edge 20. The top edge 18 has a slot 22 opening thereat. The slot 22 has a wide opening at the top edge 18 and narrows downwardly from the top edge 18.

As can be seen in FIG. 1, the slot 22 has a particular and peculiar configuration. The configuration of the slot 22 can best be described as having a dog leg shape. There is a V-shaped opening adjacent to the top edge 18 which extends to a narrow portion extending at an angle offset from the median axis of the body portion. There is another portion of the dog leg shape of the slot 22 which extends back inwardly to the median axis of the body portion 12 so as to terminate at a bottom end 24. Experimentation with this configuration shows that when the surgical tubing is forced through the slot 22 so as to reside against the terminal end 24, the surgical tubing will be firmly locked in position. This particular dog leg shape of the slot 22 will prevent any accidental release of the tubing from the slot 22.

As can be seen in FIG. 1, a plurality of fingers 26, 28, and 30 extend outwardly from the arm 14. The arm 14 extends transversely to the body portion 12 of the retractor paddle 10. Each of the fingers 26, 28, and 30 comprises a first section 32 which is connected to the arm 14 and extends transversely downwardly therefrom. A second section 34 extends transversely inwardly from an end of the first section 32 opposite the arm 14. Each of the first section 32 and the second section 34 has an interior surface 36. A plurality of ribs 38 extend outwardly from the interior surface 36. The second section 34 has an inward end 40. Each of the plurality of fingers 26, 28, and 30 has an arrowhead member 42 formed at the inward end 40. As used herein, the arrowhead member 42 will more firmly grasp the tissue in a desired manner and allow better penetration of each of the respective fingers 26, 28, and 30 into the tissue at the edge of the incision.

FIG. 2 shows another view of the retractor paddle 10. Retractor paddle 10 is shown as having body portion 12 with the arm 14 extending generally transversely therefrom. Fingers 26, 28, and 30 form the grasping surface 16 of the retractor paddle 10.

Importantly, a hole 44 is formed in the arm 14 adjacent to the connection of the arm 14 with the body portion 12. Hole 44 should have a diameter suitable for allowing surgical tubing to pass therethrough. The hole 44 is arranged so as to have a central axis extending transverse to the plane of the arm 14.

In FIG. 2, it can be seen that the slot 22 extends downwardly from the top edge 18 of the body portion 12. Importantly, an indented area 46 is formed adjacent to the bottom edge 20 of the body portion 12. Indented area 46 is configured so as to allow the surgical tubing to extend therethrough as it passed toward the hole 44.

Figure 3:
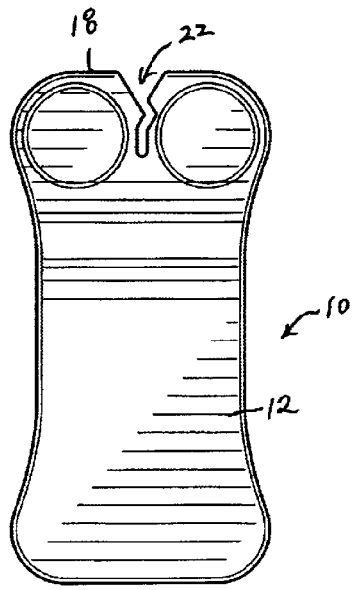
FIG. 3 is a rear view of the retractor paddle of the circumferential retractor apparatus of the present invention.

FIG. 3 shows a detailed view of the back of the body portion 12 of the retractortpaddle 10. In particular, the precise shape of the slot 22 is particularly illustrated as extending inwardly from the top edge 18 of the body portion 12. Also, in FIG. 4, a magnified view of the slot 22 is particularly illustrated. As stated earlier, the slot 22 will extend downwardly to its terminal end 24 located opposite to the top edge 18 of the body portion 12 of the retractor paddle 10. Slot 22 includes an upper V-shaped funnel area 50. Funnel area 50 opens to an inclined section 52 extending at an acute angle relative to the median axis of the body portion 12. The angled portion 52 is directed toward an offset of the median axis of the body portion 12. A return leg 54 communicates with the angled portion 52. Return leg 54 extends, at an angle, back toward the median axis of the body portion 12. Finally, a vertical portion 56 extends from the return leg 54 toward the terminal end 24. When the surgical tubing is passed through each of these areas, it will be firmly and securely received within the slot 22 such that accidental release of the tubing is effectively prevented.

FIG. 5 shows the panner in which the slot 22 effectively receives a length of surgical tubing 60. As can be seen in FIG. 5, surgical tubing 60 has an upper end which is received into the terminal end 24 of the slot 22. The tubing 60 extends downwardly through the hole formed in the arm 14 of the retractor paddle 10. The tubing 60 extends downwardly so as to extend through the indented area 46 located adjacent to the bottom 20 of the body portion 12 of retractor paddle 10.

FIG. 6 shows the circumferential retractor apparatus 70 in association with a surgical procedure. The circumferential retractor-apparatus 70 includes the retractor paddle 10 and another retractor paddle 72. In FIG. 6, it can be seen that an incision 74 is formed in a limb 76. When the incision 74 is made, the skin 78 will have one edge 80 and an opposite edge 82 which are separated. The first retractor paddle 10 is placed over the edge 82 such that the second section 34 will extend so as to be positioned adjacent to the interior surface 84 and the skin 78. The first section 32 of the grasping surface 16 would stand upwardly across the edge 82 of the incised skin 78. The arm 14 extends rearwardly from the first section 32 toward the body portion 12. The surgical tubing 60 has its end 86 extending outwardly of the body portion. The tubing 60 will extend through a space between the indented area 46 and the surface of the skin 78. The tubing 60 will then extend upwardly through the hole 44 and is then pulled upwardly and downwardly through the slot 22 such that the surgical tubing 60 can be locked within the slot 22 in the manner shown in FIG. 5.

The surgical tubing 60 extends around the limb 76. It can be seen that the second retractor paddle 74 grasps the edge 80 of the skin 78 in a similar manner as did the first retractor paddle 10. The opposite end 88 of the surgical tubing 60 is then pulled through the hole formed on the arm 90 of the retractor paddle 72 and then downwardly into a slot formed on the top edge of the retractor paddle 72 in a manner similar to that shown in FIG. 5. The surgeon can pull the end 88 of the tubing 60 to the desired degree necessary so as to create the proper tensioning for pulling the edges 80 and 82 of the skin 78 apart. The end 88 is locked into position by simply pushing downwardly so that the tubing 60 is compressively fixed in position within the terminal end 24 of the slot 22.

The surgeon can then carry out the necessary procedure within the incision 74. After surgery, the surgeon can simply pull up on either of the ends 86 and 88 of the surgical tubing 60 so as to release the surgical tubing 60 from the slots associated with the paddles 10 and 72. The surgical tubing 60 can then pull through the respective holes on the paddles 10 and 72 and be released therefrom. The retractor paddles 10 and 72 can then be simply pulled from the edges 80 and 84 of in the skin 78. The incision 74 can then be closed in a conventional manner.

The present invention achieves many advantages over conventional retractors. Since the tension applied by the tubing 60 is exterior of the incision 74, and since there is no structure above if, the incision 74 to create an obstacle to the surgical procedure, the incision 74 will be virtually free of obstacles. The unique semi-circular indentations and ribs associated with the grasping area 16 will minimize damage to the tissue incision 74. Since each of the retractor paddles 10 and 72 is formed of a polycarbonate material or a LEXAN (TM) material, each of the retractor paddles 10 and 72 is easily sterilizable or autoclavable. Preferably, in the present invention, the surgical tubing 60 and the retractor paddies 10 and 72 are simply disposed of subsequent to surgery.

The unique arrangement of the slot 22 and the hole 44, along with the indented area 46, assures that the retractor paddles 10 and 72 assume a proper orientation during the surgical procedure. As such, the combination of these elements virtually assures that the tubing 60 will not be accidentally released from its secure position within the respective paddles. Additionally, this orientation assures that the edges 80 and 82 of the skin 78 are in a proper position so as to be properly retained by the respective grasping areas of the paddles.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

We claim:

1. A circumferential retractor apparatus comprising:
    a first retractor paddle having a grasping surface, said first retractor paddle having a body portion with an arm extending outwardly therefrom, said arm supporting said grasping surface;
    a second retractor paddle having a grasping surface, said second retractor paddle having a body portion with an arm extending outwardly therefrom, said arm of said second retractor paddle supporting said grasping surface of said second retractor paddle; and
    an elastic member having one end received by said first retractor paddle and an opposite end received by said second retractor paddle, said arm of said first retractor paddle having a hole formed therein, said arm of said second retractor paddle having a hole formed therein, said elastic member having said one end extending through said hole of said first retractor paddle, said elastic member having an opposite end extending through said hole of said second retractor paddle, said body portion of said first retractor paddle having a top edge and a bottom edge, said arm extending outwardly between said top edge and said bottom edge, said body portion of said first retractor paddle having a slot opening at said top edge.

2. The apparatus of claim 1, said slot being tapered so as to have a wide opening at said top edge and narrowing downwardly therefrom.

3. The apparatus of claim 2, said slot having a dog leg shape extending downwardly from said top edge.

4. The apparatus of claim 1, said body portion of said first retractor paddle having an indented area adjacent said bottom edge, said indented area facing said arm of said retractor paddle.

5. The apparatus of claim 1, one end of said elastic member being affixed within a bottom of said slot away from said top edge.

6. A circumferential retractor apparatus comprising:
    a first retractor paddle having a grasping surface, said first retractor paddle having a body portion with an arm extending outwardly therefrom, said arm supporting said grasping surface, said grasping surface of said first retractor paddle comprising:
        a plurality of fingers extending outwardly of said arm, said arm extending generally transversely to said body portion of said first retractor paddle, each of said plurality of fingers comprising:
            a first section connected to said arm and extending generally transversely downwardly therefrom; and
            a second section extending transversely inwardly from an end of said first section opposite said arm, each of said first and second sections having an interior surface, said interior surface having a plurality of ribs extending outwardly therefrom;
    a second retractor paddle having a grasping surface, said second retractor paddle having a body portion with an arm extending outwardly therefrom, said arm of said second retractor paddle supporting said grasping surface of said second retractor paddle; and
    an elastic member having one end received by said first retractor paddle and an opposite end received by said second retractor paddle.

7. The apparatus of claim 6, said second section having an inward end, each of said plurality of fingers having an arrowhead member at said inward end.

8. The apparatus of claim 6, said elastic member being a length of surgical tubing.

9. The apparatus of claim 6, said first retractor paddle having an identical configuration to said second retractor paddle.

10. A paddle for a circumferential retractor comprising:
    a paddle member having a body portion with an arm extending outwardly therefrom, said arm supporting a grasping surface, said arm having a hole formed therein, said body portion having a slot opening at an edge thereof, said slot having a dog leg shape with a wide end at said edge.

11. The paddle of claim 10, said slot having a tapered opening at said edge, said tapered opening being wide at said edge and narrowing downwardly therefrom.

12. A paddle for a circumferential retractor comprising:
    a paddle member having a body portion with an arm extending outwardly therefrom, said arm supporting a grasping surface, said arm having a hole formed therein, said body portion having a slot opening at an edge thereof, said body portion having an indented area adjacent an opposite edge thereof, said indented area being on a side of said arm opposite said slot, said indicated area facing said grasping surface.

13. A paddle for a circumferential retractor comprising:
    a paddle member having a body portion with an arm extending outwardly therefrom, said arm supporting a grasping surface, said arm having a hole formed therein, said body portion having a slot opening at an edge thereof, said grasping surface comprising:
        a plurality of fingers extending outwardly of said arm, said arm extending generally transversely to said body portion of said paddle member.

14. The paddle of claim 13, each of said plurality of fingers comprising:
    a first section connected to said arm and extending generally transversely downwardly therefrom; and
    a second section extending transversely inwardly from an end of said first section opposite said arm.

15. The paddle of claim 14, said second section having an inward end, each of said plurality of fingers of said inward end having an arrowhead member at said inward end.

* * * * *